United States Patent
Nichiforenco et al.

(10) Patent No.: US 8,079,266 B2
(45) Date of Patent: Dec. 20, 2011

(54) DEVICE FOR TESTING MATERIAL AND MEASURING THICKNESS ON A TEST OBJECT HAVING AT LEAST ELECTRICALLY CONDUCTING AND FERROMAGNETIC MATERIAL PARTS

(75) Inventors: Jorj Nichiforenco, Saarbrücken (DE); Andrei Bulavinov, Saarbrücken (DE); Michael Kröning, Saarbrücken (DE)

(73) Assignee: Fraunhofer-Gesellschaft zur Förderung der Angewandten Forschung E.V., Munich (DE)

( * ) Notice: Subject to any disclaimer, the term of this patent is extended or adjusted under 35 U.S.C. 154(b) by 931 days.

(21) Appl. No.: 11/718,911

(22) PCT Filed: Nov. 8, 2005

(86) PCT No.: PCT/EP2005/011949
§ 371 (c)(1),
(2), (4) Date: Mar. 7, 2008

(87) PCT Pub. No.: WO2006/050914
PCT Pub. Date: May 18, 2006

(65) Prior Publication Data
US 2008/0276711 A1    Nov. 13, 2008

(30) Foreign Application Priority Data
Nov. 10, 2004 (DE) .......... 10 2004 054 423

(51) Int. Cl.
*G01N 29/24* (2006.01)
*G01N 29/265* (2006.01)
(52) U.S. Cl. .......... 73/643
(58) Field of Classification Search .......... 73/643
See application file for complete search history.

(56) References Cited

U.S. PATENT DOCUMENTS

| | | | |
|---|---|---|---|
| 3,668,517 A * | 6/1972 | Zemberry | 324/216 |
| 3,697,867 A | 10/1972 | Kleesattel | |
| 3,771,354 A | 11/1973 | Miller | |
| 4,164,873 A * | 8/1979 | Bottcher et al. | 73/643 |
| 4,898,034 A | 2/1990 | Kupperman et al. | |
| 7,024,935 B2 * | 4/2006 | Paige et al. | 73/643 |

FOREIGN PATENT DOCUMENTS

| | | | |
|---|---|---|---|
| EP | 722085 A1 * | 7/1996 | |
| GB | 1 561 811 | 3/1980 | |
| JP | 11133003 A | 10/1997 | |

OTHER PUBLICATIONS

Clark, R.: "Rail Flaw Detection: Overview and Needs for Future Developments", NDT & E International, Butterworth-Heinemann, Oxford, GB, vol. 37, No. 2, Mar. 2004, pp. 111-118, XP004481709, ISSN: 0963-8695.

* cited by examiner

*Primary Examiner* — Hezron E Williams
*Assistant Examiner* — Rose M Miller
(74) *Attorney, Agent, or Firm* — Antonelli, Terry, Stout & Kraus, LLP.

(57) ABSTRACT

A device is disclosed for material testing on a test object having at least electrically conducting and ferromagnetic material parts. The test object has at least one technical surface on which at least one electromagnetic ultrasonic transducer (EMUS) is rolled. The at least one transducer includes at least one permanent magnet or an electromagnet and at least one eddy current coil. The at least one eddy current coil has at least one electrical strip conductor which is disposed at or parallel to a surface area of a rolling member which can be rolled on the technical surface of the test object, with the surface area rolling along with the rolling member during rolling.

17 Claims, 3 Drawing Sheets

DEVICE FOR TESTING MATERIAL AND MEASURING THICKNESS ON A TEST OBJECT HAVING AT LEAST ELECTRICALLY CONDUCTING AND FERROMAGNETIC MATERIAL PARTS

BACKGROUND OF THE INVENTION

1. Field of the Invention

The present invention relates to a device for testing material on a test object having at least electrically conducting and ferromagnetic material parts, the test object having at least one technical surface with at least one electromagnetic ultrasonic transducer (EMUS) provided with at least one magnet and at least one eddy current coil.

2. Description of the Prior Art

Electromagnetic ultrasonic transducers are used in a known manner for the purpose of non-destructive material testing and measurement of test objects comprising electrically conducting materials which moreover possess ferromagnetic properties.

Basically electromagnetic ultrasonic transducers can be differentiated into two types: on the one hand, those with which produce so-called horizontally polarized shear waves which are able to propagate inside the test object predominantly parallel to the coupling-in surface; and on the other hand, ultrasonic transducers for generating in the test object so-called freely propagating ultrasonic waves preferably propagating inside the test object perpendicular to the coupling-in surface. In both instances, excitation of ultrasonic waves inside a test object results from the occurrence of magnetostriction and Lorenz forces inside the test object material, which can be generated by the presence of a temporally largely constant magnetic field overlapping with an electromagnetic alternating field generated by an electromagnetic alternating current.

A typical setup for exciting ultrasonic waves according to the so-called EMUS principle is shown in FIGS. 8a and 8b. Common EMUS transducers 3 comprise a permanent magnet 1 and an eddy current coil 2, which are designed as one unit for joint handling. Usually the eddy current coil 2 is designed as a rectangular flat coil or a spiral flat coil each of which have an electrically conductive strip and is attached to a magnetic pole side of the permanent magnet 1 in such a manner that a permanent magnetic field passes vertically through the coil 2. If the aforementioned EMUS transducer 3 is placed on an electrically conducting ferromagnetic test object 4, the permanent magnetic field overlaps inside the test object with an eddy current field generated by the eddy current coil, on the one hand, generating magnetostrictive effects due to the overlapping of the magnetic field components of the eddy current field with the permanent magnetic field entering vertically through the surface of the test object and, on the other hand generating the Lorenz forces due to the eddy currents induced in the test object, which then generate pressure waves occurring normally in relation to the surface of the test object as well as radially polarized shear waves capable of propagating as ultrasonic waves inside the test object. Both types of ultrasonic waves, that is the ultrasonic waves propagating normally in relation to the surface of the test object and ultrasonic waves propagating in longitudinal direction to the surface of the test object due to radially polarized shear waves are suited according to the state of the art for testing faults, for example detecting cracks inside the test object, as well as for measuring the thickness of the wall of the test object.

Since in use eddy current coils are very sensitive to outside mechanical influences, the eddy current coils must principally be protected against mechanical wear, which is difficult in particular due to the fact that in ferromagnetic test objects the eddy current coil located between the permanent magnet and the test object is pressed onto the surface of the test object by the magnetic forces of attraction and is therefore subject to considerable fretting.

In this context, German Patent 35 11 076 A1 describes a test pig for electromagnetic testing of the walls of steel pipes, such as, for example as part of nondestructive testing of wall weaknesses due to rusting of the pipe walls. A pig, which is described in detail therein, is provided with electromagnets, which are distributed uniformly around the circumference, each comprising two measuring heads which are axially aligned to each other, a yoke connecting the measuring heads and a magnetizing coil on the measuring heads, with the field of each electromagnet running parallel to the center axis of the pipe. For ultrasonic measurement, an eddy current coil, to which are applied strong and very rapidly rising current pulses, is disposed directly at least on one of the poles, and the measuring heads. The pipes of pipelines are provided with circumferential seams at the adjoining parts of two adjacent pipe pieces. When the above briefly described test pig runs over the seams during continuous inspection, the circumferential seams subject the electromagnetic transducer to impacts which, moreover, are markedly intensified by the magnetic forces prevailing between the electromagnets and the wall of the pipes. The previously described fretting and the additional impacts to the electromagnetic ultrasonic transducer, in particular to the eddy current coil, lead to a short lifetime of the EMUS transducer, which needs to be addressed.

Although fretting can be reduced by decreasing the magnetic forces of attraction prevailing between the EMUS transducer and the to-be-inspected test object, for example by decreasing the magnetic field induction, this measurement would also immediately lead to distinctly diminishing the EMUS transducer's efficiency, that is force density induced to generate ultrasound inside the test object reduces in the same way, due to which the detection sensitivity in receiving scattered or reflected ultrasonic waves diminishes to the same extent.

Japanese Patent 111 33 003 describes a device for inspecting material using ultrasound which is suited in particular for inspecting the material of pipes. According to claim 4 therein, the device comprises single permanent magnets which are arranged to form a ring of segments with an outer and an inner circumferential edge. The adjacent permanent magnets have opposite magnetic poles at the outer and inner circumferential edge. Disposed in windings on the outer circumferential edge of this ring is an electrical strip conductor of at least one eddy current coil. The device is introduced in operation into a pipe that the outer circumferential edge with the strip conductors slides along the inner wall of the pipe, leading to corresponding fretting on the strip conductors.

U.S. Pat. No. 4,898,034 describes a device for testing hot materials, such as metals and ceramics, using ultrasound. An embodiment uses an agent made of zircon which is in contact with the hot material to be examined. Furthermore, a coupling medium (borax) is in contact with the hot material and the zircon agent. The zircon agent and the coupling medium receives ultrasonic waves propagating from the hot material through the coupling medium and the zircon agent. In the embodiment shown in FIG. 1 of U.S. Pat. No. 4,898,034, the zircon agent is designed as a ring with an outer and an inner circumferential edge. In operation, the outer circumferential edge of the ring is rolled over the hot material to be examined. A lever, which is attached to the rotational axis of the zircon ring, holds the ultrasound transmitter constantly as shown in downward perpendicular position. In this manner the ultrasound transmitter including the eddy current coil attached to it is pressed against the inner circumferential edge of the ring, leading once again to fretting of the ultrasound transmitter.

SUMMARY OF THE INVENTION

The present invention is a device for material testing of a test object having at least electrically conducting and ferromagnetic material parts based on electromagnetic ultrasonic excitation and using an electromagnetic ultrasonic transducer array (EMUS) so that eddy current coils required for generating eddy currents are not subject to any or minimum fretting. Furthermore, conducting material testing on the test object continuously is possible.

Contrary to the usual electromagnetic ultrasonic transducer arrays which are provided with permanent magnets or electromagnets and at least one eddy current coil and in which the eddy current coil is moved in a sliding manner in order to inspect the material at the surface of a test object and therefore are subject to slip friction wear, the electromagnetic ultrasonic transducer according to the present invention provides a new eddy current coil design which is combined with a rolling member which is rolled over the surface of a test object. The electromagnetic ultrasonic transducer, hereinafter EMUS transducer, according to the present invention is subject to less wear compared to standard versions. The rolling friction forces occurring in the EMUS transducer according to the present invention are substantially less than the slip friction forces which considerably increases the lifetime of the EMUS transducer according to the present invention.

If a prior art EMUS transducer is moved by slipping over an uneven surface of a test object in a slipping process, the eddy current coil therein is subject to increased wear due to the unevenness of the surface of the test object, such as, for example, due to bulging at the welding seams. With the EMUS transducer according to the present invention, surface unevenness is simply rolled over without lasting impairment of the eddy current coil.

Another advantage of the EMUS transducer according to the present invention is conducting material inspection continuously as will be described in detail in the following.

Thus a device for testing material on a test object which comprises at least electrically conducting and ferromagnetic material parts and which possesses at least one technical surface having an electromagnetic ultrasonic transducer provided with a magnet which is permanent or an electromagnet and at least one eddy current coil according to the invention includes at least one eddy current coil having at least one electrical strip conductor which is disposed at or parallel to a surface area of a rolling member which is disposed on the technical surface of the test object which can be rolled over.

In a particularly preferred embodiment, the rolling member, which preferably is a disk, reel, wheel or ball, is combined with the permanent magnet or electromagnet in such a manner that the rolling member, the permanent magnet or electromagnet as well as the at least one eddy current coil which is attached on the rolling member or connected to the rolling member, is moved uniformly in relation to the test object.

Another preferred embodiment provides for separate handling of the at least one permanent magnet or electromagnet and the combination of rolling member and eddy current coil.

Further details to the preferred embodiments are described in the following with reference to the accompanying figures.

BRIEF DESCRIPTION OF THE DRAWINGS

The present invention is made more apparent in the following by way of example using preferred embodiments with reference to the accompanying drawings without the intention of limiting the scope or spirit of the invention.

DETAILED DESCRIPTION OF THE INVENTION

Figure 1:
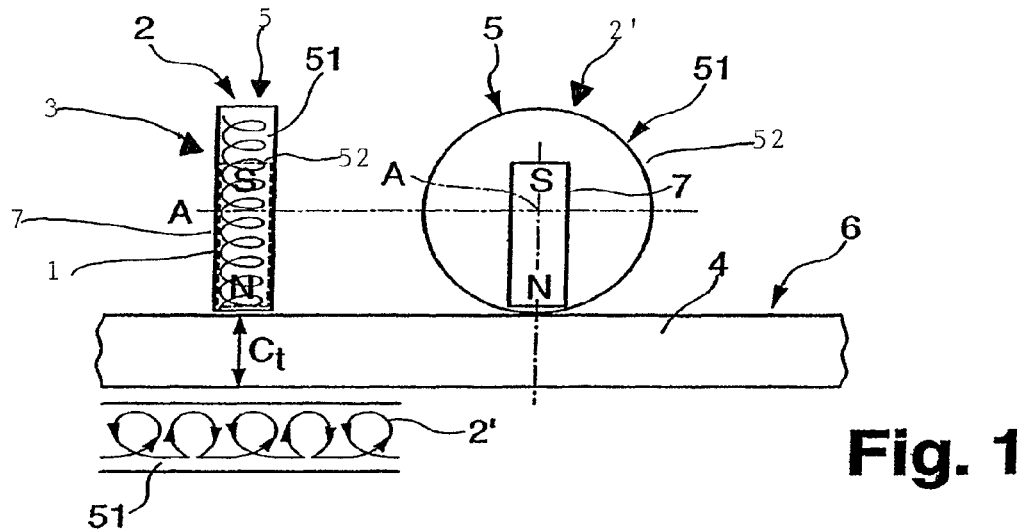
FIG. 1 shows a schematic representation of EMUS transducers having a permanent magnet and an eddy current coil with elliptically shaped strip conductor loops, attached to the circumferential edge of a rolling member.

The left representation in FIG. 1 shows a front view and the right representation shows a lateral view, of the EMUS transducer according to the present invention, which due to its principle of construction is also referred to as an EMUS wheel. The EMUS transducer is provided with a rolling member 5 which in the preferred embodiment is designed to be a ring or reel which is hollow inside and has an outer circumferential edge 51. The rolling member 5 has a center axis of rotation A about which the rolling member 5 rolls relative to the technical surface 6 of the test object 4. An eddy current coil 2 is wound along the circumferential edge 51 of the rolling member 5 as shown in the left representation. The eddy current coil 2 comprises a through-going electrical conductor including elliptical strip conductor loops 52 which are wrapped along the circumferential edge 51 of the rolling member 5 in such a manner that the entire circumferential edge 51 of rolling member 5 is covered by the loops 52. It is obvious that when the current is applied to the strip conductors 52, two immediately adjacent strip conductor loops 52 have current flowing in opposite directions. The alternative strip conductors 52' are wound on the circumferential so that two strip conductors wound immediately adjacent to each other extend in the same direction. The strip conductor 52 and 52' are each suited for effectively coupling in ultrasonic waves into the test object 4.

Each EMUS transducer shown in FIG. 1 is provided with a permanent magnet 7 to introduce a temporally constant magnetic field into the test object. The permanent magnet 7 is attached to the axis of rotation A in such an asymmetrical manner that a magnetic pole, preferably the magnetic north pole N is disposed maximally close to the circumferential edge 51 of the rolling member 5. When the rolling member rolls along the technical surface 6 of the object 4, the magnetic north pole N of the permanent magnet 7 is drawn to the ferromagnetic test object 4 and, due to its rotational mobility, about the axis of rotation A always stays facing the test object 4, so that the magnetic north pole is always directed downward. Thus the permanent magnet 7 generates a magnetic field whose magnetic field lines are always oriented perpendicular to the technical surface 6 of the test object 4.

If the eddy current coil 2 is fed with pulsed current, eddy currents are induced in the test object which interact with the magnetic flow oriented normally to the technical surface 6. Ultrasonic waves with circular polarization are generated in test object 4 by developing Lorenz forces. The ultrasonic waves propagate essentially perpendicular to the technical surface 6 inside the test object 4.

The eddy current coil 2 also functions as a reception coil for the ultrasonic waves reflected back inside the test object 4.

Figure 2:
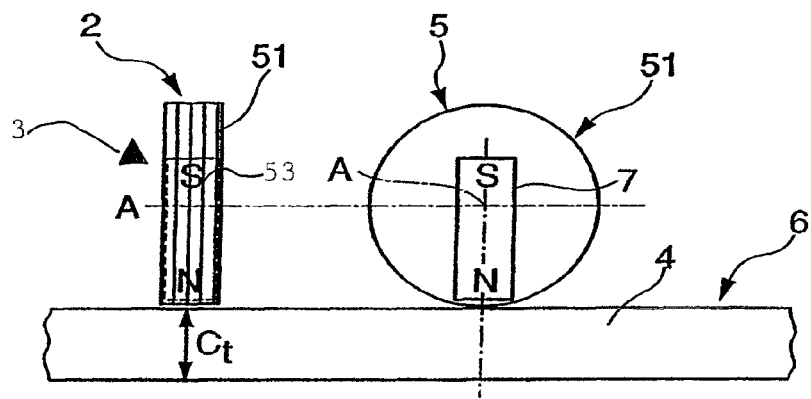
FIG. 2 shows a schematic representation of an EMUS transducer having a permanent magnet and an eddy current coil with a strip conductor windings at the circumferential edge of a rolling member.

As an alternative to the strip conductors of the eddy current coil 2 depicted in FIG. 1, FIG. 2 shows a variant of the EMUS transducer in which the eddy current coil 2 has electrical windings 53 which are each disposed around the circumferential edge 51 of the rolling member 5. The design of the strip conductors 53 of the current coil 2 is shown in the left representation of FIG. 2. Due to the alternative embodiment of the strip conductors 53 according to the preferred embodiment in FIG. 2, ultrasonic waves with linear polarization are generated in the test object 4. The ultrasonic waves however are due to the same excitation principle by Lorenz forces occurring as in the preferred embodiment according to FIG. 1.

In both preceding embodiments of FIGS. 1 and 2, the rolling member 5 is preferably not a metallic material. The rolling member 5 can, of course, also be made of a ferromagnetic and electrically conductive material. In this case, however, care must be taken that the strip conductors 52 or 53 of the eddy current coil 2 are electrically insulated from the rolling member 5. It is also expedient, for further reduction of the rolling friction occurring between the rolling member 5 and the technical surface 6, to provide a protective coat (not depicted) to protect the eddy current coils 52 or 53.

Figure 3:
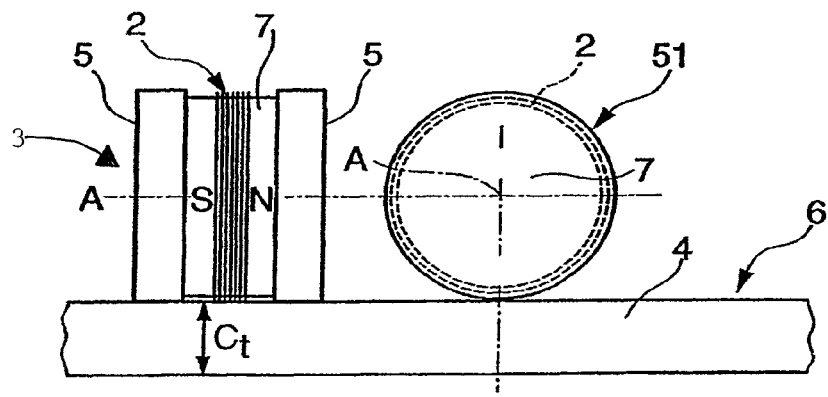
FIG. 3 shows a schematic representation of an EMUS transducer having a permanent magnet and two ferromagnetic return paths.

In contrast to the preceding preferred embodiments of FIGS. 1 and 2 in which a temporally constant magnetic field is oriented perpendicular to the technical surface 6 of the test object 4 and is coupled into the test object 4, the preferred embodiment of an EMUS transducer designed according to the invention depicted in FIG. 3 causes a magnetic field to be coupled into the technical surface 6, which is oriented tangentially to the technical surface of test object 4. FIG. 3 shows again in the left representation, a front view and in the right representation, a lateral view of the EMUS transducer 3. In the preferred embodiment, the strip conductors of the eddy current coil 2 are wound around the surface of a cylindrical or rod-shaped permanent magnet 7. Attached at the opposite N and S magnetic poles of the permanent magnet 7 are two disk rolling members 5 composed of ferromagnetic material, which is preferably a ferrosteel and which project radially outward from the axis of rotation of the permanent magnet 7 including the eddy current 2. The disk rolling members 5 each act as a yoke which conducts the magnetic field lines so that a magnetic circuit including the ferromagnetic rolling members 5 and the test object is closed. Due to the magnetic return path, a magnetic field is coupled tangentially to the technical surface 6 inside test object 4. The eddy currents excited by the eddy current coils 2 generate inside the test object 4 a secondary alternating magnetic field which overlaps with the constant magnetic field of the permanent magnet 7. The ultrasonic waves are excited by the developing magnetostrictive effect and, like in the case of the embodiment according to FIG. 2, have a linear polarization. The disk rolling members 5, which enclose the permanent magnet 7 on both sides, have two functions. On the one hand the rolling members 5 act as a magnetic yoke and on the other hand they permit the ultrasonic transducers to roll over the technical surface 6 of the test object 4, with the eddy current coils 2 always assume a constant distance from the technical surface 6, due to which the strip conductors are subject to no mechanical wear from rolling friction.

Figure 4:
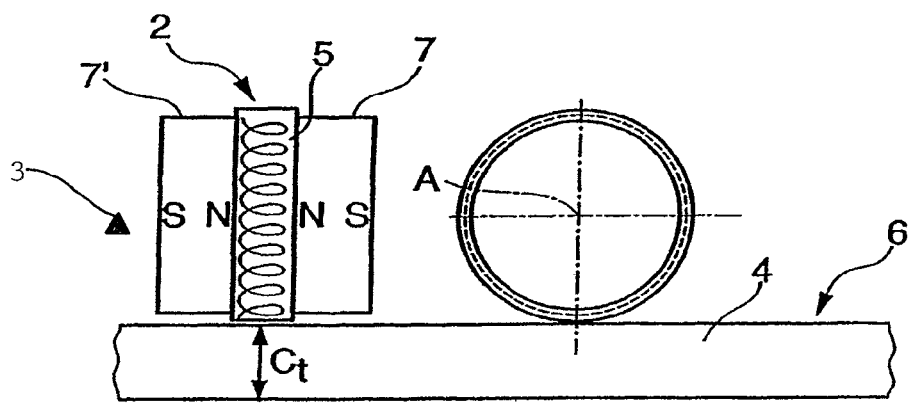
FIGS. 4 and 5 show a view of an EMUS transducer having two permanent magnets and an eddy current coil.
Figure 5:
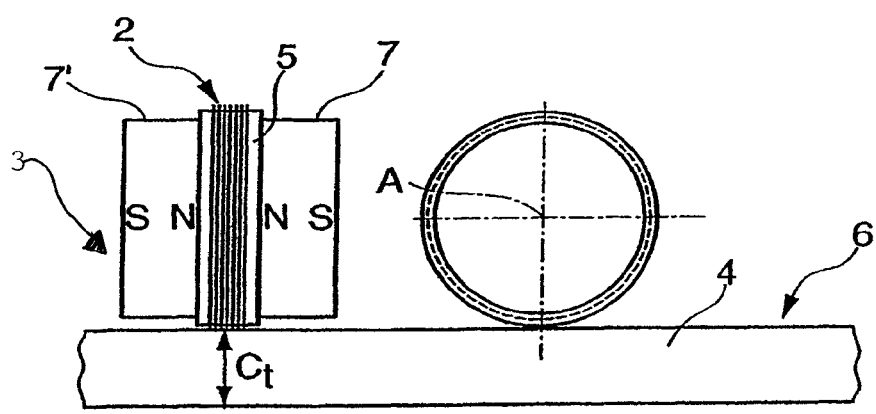

FIGS. 4 and 5 show two further preferred embodiments of an EMUS transducer 3 according to the invention. These embodiments are provided with two permanent magnets 7 and 7' and an eddy current coil 2. The only difference in the designs of the two embodiments is in the eddy current coils 2. The permanent magnets 7 and 7' are attached with their opposing magnetic north poles N to the ferromagnetic rolling member 5, which preferably is a ring or a wheel. Due to the opposite magnetic north poles N, a displacement of the magnetic field lines occurs in such a manner that they are coupled, via the ferromagnetic ring unit rolling member 5, perpendicular to the technical surface 6 of the test object 4. The ferromagnetic rolling member 5 acts simultaneously as a concentrator of the magnetic field by which the magnetic field at the contact points between the rolling member 5 and the technical surface 6 is coupled into the test object 4 in a concentrated manner. Moreover, the ultrasonic-wave excitation principle is the same as in the preferred embodiments in FIGS. 1 and 2.

In order to improve closure of the magnetic circuit in the preferred embodiments shown in FIGS. 4 and 5, a ferromagnetic end piece may be provided on the front magnetic south poles, which like the rolling member 5 comes into contact with the technical surface 6 of the test object 4.

Figure 6:
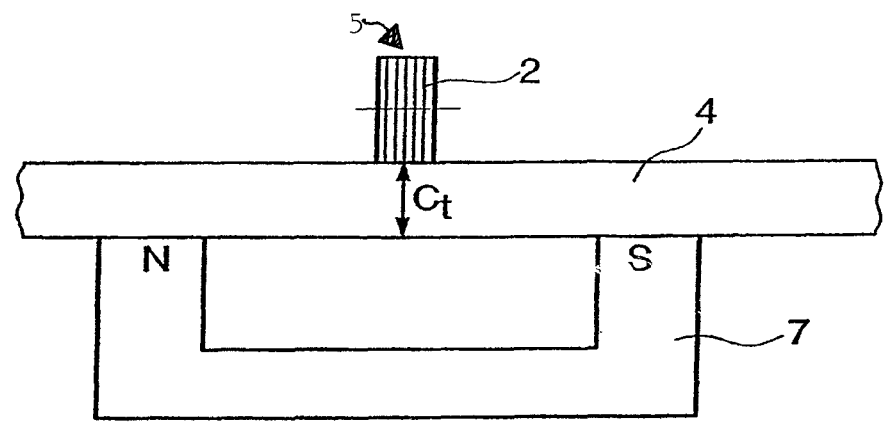
FIGS. 6 and 7 show a representation of an EMUS transducer having an electromagnet and a separate eddy current coil.
Figure 7:
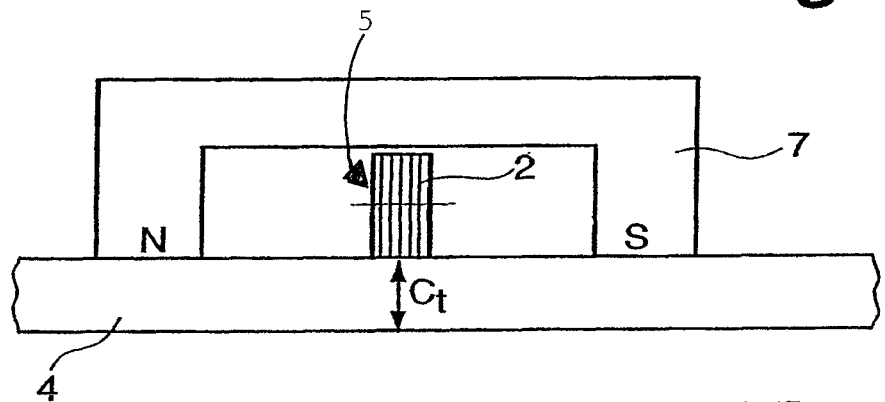
Figure 8:
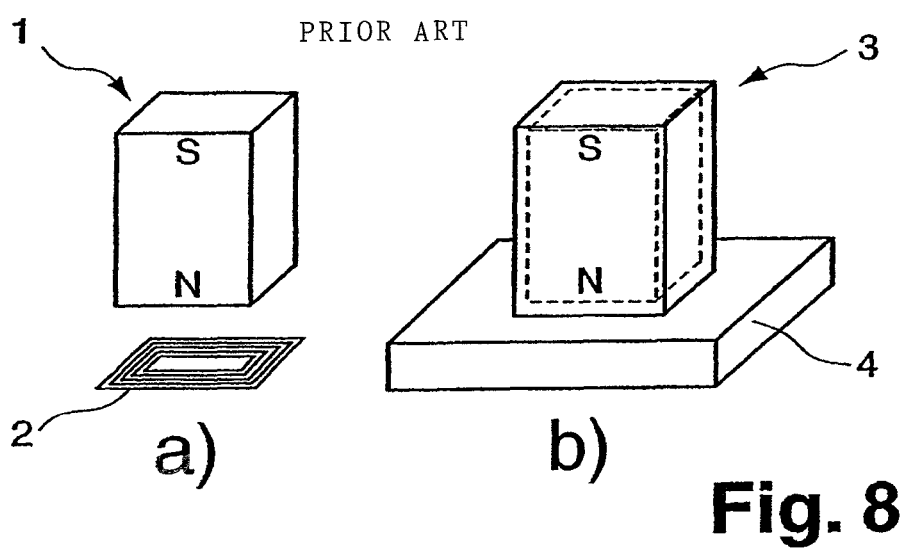
FIGS. 8a and b show a prior art EMUS transducer.

In some material testing applications using permanent magnets can be obviated, as for example material with testing on sheet metals. In this case electromagnets are preferable. FIGS. 6 and 7 show preferred embodiments each with separate arrangement between the electromagnet 7 and the eddy current coils 2. The yoke-shaped electromagnet array 7 has two magnetic poles N and S which each can be placed on the technical surface 6 of the test object 4 to feed a tangential magnetic field. Provided in the area of the tangential magnetic field is a rolling member 5 at whose circumferential edge an eddy current coils 2 are provided. In the example of the FIG. 6, the rolling member 5 is located on a top side of the test object facing away from the electromagnet array 7. In the example according to FIG. 7, both the electromagnet array 7 and the rolling member 5 are located on a common technical surface 6 of the test object 4. The excitation principle of the ultrasonic waves inside the test object 4 is identical to that according to the preferred embodiment in FIG. 3. The tangentially running magnetic field which is fed by the electromagnet 7 into the test object 4 interacts with the eddy currents and the alternating magnetic field in such a manner that, due to the occurrence of magnetostrictive effects, linear polarized ultrasonic waves are generated. Of course, eddy current coils 2, designed as rolling members 5, can be provided in the area of the tangential magnetic field. As in the preferred embodiments shown in FIGS. 6 and 7, since no magnetic attraction forces act between the rolling member 5 and the technical surface 6 of the test object 4, wear of the EMUS transducer is minimal.

Rolling the rolling member 5 along the circumferential edge on which the eddy current coils are disposed uniformly allows conducting continuous inspection in contrast to the hitherto used locally discrete EMUS testing arrangements. The invention, also referred to as EMUS wheel, is fundamentally suitable for an application to different fields such as for measuring the wall thickness and fault inspection of sheet metals, rails, pipes and pipelines as well as railroad wheels, oil containers or the outer walls of ships and other security containers. The EMUS transducer can also be combined with transport systems, for example so-called pig systems used in long-distant pipelines and the like to perform inspection.

LIST OF REFERENCES 1 permanent magnet
2 eddy current coil
3 EMUS transducer
4 test object
5 rolling member
6 technical surface
7 permanent magnet

The invention claimed is:

1. A device for material testing of a test object including at least one surface and at least electrically conducting and ferromagnetic parts comprising:
   at least one electromagnetic ultrasonic transducer including at least one magnet and at least one eddy current coil; and wherein
   the at least one eddy current coil has at least one electrical strip conductor disposed at or parallel to a surface area of a ferromagnetic or electrically conductive rolling member for rolling on the at least one surface of the test object, with the surface area and the rolling member rolling over the at least one surface, the at least one magnet is integrated in the rolling member and moves jointly with the rolling member relative to the at least one surface to cause a magnetic field from the at least one magnet to penetrate at least into one area of the test object which is in contact with the rolling member when the rolling member rolls over the at least one surface, and the rolling member is a disk or cylinder having a circumferential edge around which the at least one electrical strip conductor of the eddy current coil is curved, the rolling member has an axis of rotation about which the rolling member rotates when rolling on the surface of the test object, and the at least one magnet is a bar permanent magnet which is attached asymmetrically and is rotatable about the axis of rotation of the rolling member so that a mass center of gravity of the bar permanent magnet lies outside the axis of rotation and a magnetic pole of the bar permanent magnet continually faces the circumferential edge of the rolling member during rolling contact with the surface of the test object.

2. The device according to claim 1, wherein:
   the at least one strip conductor is at least one winding wound around the circumferential edge of an electrical conductor to which alternating current can be applied.

3. The device according to claim 2, wherein:
   the at least one strip conductor has strip conductor windings formed of a continuous electrical conductor and disposed side by side along the circumferential edge of the rolling member.

4. The device according to claim 3, wherein:
   the strip conductor windings are loops disposed along the circumferential edge of the rolling member so that in two directly adjacent conductor sections current flows therein in the same direction.

5. The device according to claim 3, wherein:
   the strip conductor windings are loops disposed along the circumferential edge of the rolling member so that in two directly adjacent conductor sections current flows therein in opposite directions.

6. The device according to claim 1, wherein:
   the permanent magnet is rotatably disposed inside the rolling member, which is hollow inside, so that a magnetic pole of the permanent magnet extends inside the rolling member adjacent the circumferential edge.

7. A device for material testing of a test object including at least one surface and at least electrically conducting and ferromagnetic parts comprising:
   at least one electromagnetic ultrasonic transducer including a pair of magnets and at least one eddy current coil; and wherein
   the at least one eddy current coil has at least one electrical strip conductor disposed at or parallel to a surface area of a ferromagnetic or electrically conductive rolling member for rolling on the at least one surface of the test object, with the surface area and the rolling member rolling over the at least one surface, the pair of magnets is integrated in the rolling member, which move with the rolling member relative to the at least one surface to cause a magnetic field from the pair of magnets to penetrate at least into one area of the test object which is in contact with the rolling member when the rolling member rolls over the at least one surface, the rolling member is a disk or cylinder having a circumferential edge around which the at least one electrical strip conductor of the eddy current coil is curved, the rolling member has an axis of rotation about which the rolling member rotates when rolling on the surface of the test object, and the pair of magnets includes magnets with identical magnetic poles positioned opposite each other adjacent to the rolling member.

8. The device according to claim 7, wherein:
   wherein the magnets are provided with north magnetic poles disposed directly or indirectly opposite each other;
   the rolling member is disposed between the north magnetic poles or at least partially surrounds the north magnetic poles; and
   the rolling member has a larger radial extension oriented about the axis of rotation than the magnets.

9. A device for material testing of a test object including at least one surface and at least electrically conducting and ferromagnetic parts comprising:
   at least one electromagnetic ultrasonic transducer including at least one magnet and at least one eddy current coil; and wherein
   the at least one eddy current coil has at least one electrical strip conductor disposed at or parallel to a surface area of a ferromagnetic or electrically conductive rolling member comprising a pair of disks or cylinders for rolling on the at least one surface of the test object, with the surface area and the rolling member rolling over the at least one surface, the at least one magnet comprises a cylindrical or rod-shaped permanent magnet including a surface at least in an area of the at least one strip conductor of the eddy current coil; at magnetic poles of the permanent magnet the disks or cylinders are attached to an axis of rotation of the rolling member within the disks or rollers and an outer radius of the rolling member is greater than an outer radius of the permanent magnet and an outer radius of the at least one strip conductor.

10. The device according to claim 9, wherein:
    the at least one strip conductor is at least one winding wound around the circumferential edge of an electrical conductor to which alternating current can be applied.

11. The device according to claim 9, wherein:
    the at least one strip conductor has strip conductor loops formed from a continuous electrical conductor and is disposed side by side in the circumferential direction relative to the surface of the permanent magnet.

12. The device according to claim 11, wherein:
the strip conductor loops are disposed along the surface of the permanent magnet so that in two directly adjacent conductor sections current flows in a same direction.

13. The device according to claim 11, wherein:
the strip conductor loops are disposed along a surface of the permanent magnet so that current flows through two directly adjacent conductor sections in opposite directions.

14. A device for material testing of a test object including at least one surface and at least electrically conducting and ferromagnetic parts comprising:
at least one electromagnetic ultrasonic transducer including at least one magnet and at least one eddy current coil; and wherein
the at least one eddy current coil has at least one electrical strip conductor disposed at or parallel to a surface area of a ferromagnetic or electrically conductive rolling member for rolling on the at least one surface of the test object, with the surface area and the rolling member rolling over the at least one surface, the at least one magnet is U-shaped and includes magnetic poles facing the at least one surface for coupling a magnetic field oriented parallel to the at least one surface into the test object, the rolling member is a disk or cylinder including a circumferential edge around which the at least one strip conductor of the eddy current coil is curved, and the at least one strip conductor comprises at least one winding.

15. A device for material testing of a test object including at least one surface and at least electrically conducting and ferromagnetic parts comprising:
at least one electromagnetic ultrasonic transducer including at least one magnet and at least one eddy current coil; and wherein
the at least one eddy current coil has at least one electrical strip conductor disposed at or parallel to a surface area of a ferromagnetic or electrically conductive rolling member for rolling on the at least one surface of the test object, with the surface area and the rolling member rolling over the at least one surface, the at least one magnet is U-shaped and includes magnetic poles facing the at least one surface for coupling a magnetic field oriented parallel to the at least one surface into the test object, the rolling member is a disk or cylinder having a circumferential edge around which the at least one strip conductor of the eddy current coil is curved, and the at least one strip conductor is a strip conductor comprising loops of continuous electrical conductor with individual loops being disposed side by side along the circumferential edge of the rolling member.

16. The device according to claim 15, wherein:
the strip conductor loops are disposed along the circumferential edge of the rolling member so that through two directly adjacent conductor sections current flows in the same direction.

17. The device according to claim 15, wherein:
the strip conductor loops are disposed along the circumferential edge of the rolling member so that current flows in opposite directions in two directly adjacent conductor sections.

* * * * *